United States Patent [19]

Tsujita et al.

[11] Patent Number: 4,871,396
[45] Date of Patent: Oct. 3, 1989

[54] GRANULAR COMPOSITION AND DENTIFRICE CONTAINING THE SAME

[75] Inventors: Satoshi Tsujita; Koji Maeda; Yasuteru Eguchi, all of Utsunomiya, Japan

[73] Assignee: Kao Corporation, Tokyo, Japan

[21] Appl. No.: 119,559

[22] Filed: Nov. 12, 1987

[30] Foreign Application Priority Data

Nov. 25, 1986 [JP] Japan ................................ 61-280331

[51] Int. Cl.$^4$ ............................................. C09D 1/00
[52] U.S. Cl. .................................. 106/286.8; 106/35; 106/462; 106/463; 106/464; 106/467; 106/468; 424/49; 424/57; 433/216
[58] Field of Search ....................... 106/35, 286.8, 462, 106/463, 464, 467, 468; 252/174.25; 424/49, 57; 433/216

[56] References Cited

U.S. PATENT DOCUMENTS

| | | | |
|---|---|---|---|
| 3,767,791 | 10/1973 | Cordon et al. | 424/49 |
| 3,946,108 | 3/1976 | Tomlinson et al. | 424/49 |
| 3,955,942 | 5/1976 | Cordon et al. | 424/49 |
| 3,956,478 | 5/1976 | King et al. | 424/49 |
| 4,002,732 | 1/1977 | Gault | 424/49 |
| 4,003,971 | 1/1977 | Mannara | 264/9 |
| 4,069,312 | 1/1978 | Mannara | 424/49 |
| 4,209,504 | 1/1080 | Harth et al. | 424/49 |
| 4,344,931 | 8/1982 | Aguilar | 424/49 |
| 4,428,928 | 1/1984 | Muhler et al. | 424/49 |
| 4,527,979 | 7/1985 | McLean et al. | 106/35 |
| 4,576,922 | 3/1986 | O'Brien et al. | 106/35 |
| 4,626,514 | 12/1986 | Watanabe et al. | 106/35 |
| 4,632,826 | 12/1986 | Plöger et al. | 424/49 |

Primary Examiner—Paul Lieberman
Assistant Examiner—Willie J. Thompson
Attorney, Agent, or Firm—Oblon, Spivak, McClelland, Maier & Neustadt

[57] ABSTRACT

A novel granular composition comprises a water-insoluble powder material and a water-insoluble inorganic binder capable of binding said water-soluble powder material. Granules in the composition have a specific diameter and collapse under a load of 0.1–10 g per one grain of granule. The granular composition is preferably incorporated into a dentifrice, and granules incorporated therein can be recognized as granules in the mouth, however, polishing effect of the teeth can be acknowledged with almost no unpleasant feel of foreign substance.

14 Claims, 2 Drawing Sheets

GRANULAR COMPOSITION AND DENTIFRICE CONTAINING THE SAME

BACKGROUND OF THE INVENTION

1. Field of the Invention

This invention relates to a granular composition for dentifrices, which is capable of giving an aesthetic effect to them and of being recognized its cleansing effect by the sensation of collapsing granules in the mouth. More particularly, this invention relates to a granular composition which will never give an unpleasant feel of foreign matter, though the granules incorporated in a dentifrice composition maintain such a strength that can be perceived as granules in the mouth, and will collapse slowly along the process of brushing the teeth. The invention also relates to a dentifrice composition comprising said granular composition.

2. Description of the Prior Art

It is known that dentifrice compositions are sometimes blended with granules or granule-like materials. The granules are generally prepared to contain functional substances such as medicaments, enzymes and polishers, or are incorporated in dentifrice compositions with a purpose of giving an aesthetic appreciation to the products. Some conventional dentifrice compositions contain a granular composition whose shape can be recognized in the mouth immediately after starting brushing but can no more be recognized along the brushing process, or cannot be recognized at all from the very beginning of the brushing. In the last case, the cleansing effect can only be confirmed with the eyes. Conventional binders of the granules are divided into two groups of water-soluble and water-insoluble substances. Examples of the water-soluble granular binders currently on use are certain polymer compounds including methyl cellulose and carboxymethyl cellulose. These water-soluble binders are good for granular compositions which are to be prepared into dry products of medicaments or the like. However, when they are incorporated in a composition containing much water such as dentifrices and facial cleansing cosmetics, the solidity of the granules significantly decreases and will collapse during the mixing process of manufacture or, even if collapsing is narrowly avoided, the granular shape can no more be maintained because of the humidity, and if ever maintained, the granular touch will never be sensed in the mouth, leading to unablement of recognizing cleansing effects contributed to the granules.

To solve the above problems, it has been proposed, among others, to use a variety of water-insoluble organic binders, which include a method disclosed in Japanese patent application Kokai Nos. 132249/1974 and 81594/1975 where wax blended with a pigment is made into a granular composition and a method disclosed in Japanese patent application Kokai No. 126906/83 where a powder of calcium carbonate or the like is prepared into granules by the use of a binder which is water-insoluble but soluble in ethanol. These granules, however, are still unsatisfactory in that when prepared to have such a solidity and size that will ensure the palpability of granules in the mouth, they give an unpleasant sensation of foreign matter though they are stable in the dentifrice composition. Moreover, concerning the aforementioned method of using wax, there is a difficulty in that ordinary granule formation methods of wet extrusion granulation method and spray-dry method are not appropriate in the practice. On the other hand, the method of using ethylcellulose dissolved in an organic solvent is accompanied by potential danger of fire, so that special fire-prevention devices and skilled operation are required.

SUMMARY OF THE INVENTION

The present inventors made extensive studies regarding the aforementioned granular compositions suitably usable for dentifrices as well as dentifrice compositions containing such granules, and found that a dentifrice composition blended with granules which are prepared by binding a water-insoluble powder material by the use of a water-insoluble binder and are capable of maintaining a certain degree of strength can give almost no unpleasant feel of foreign mater, although the granules contained therein are palpable in the mouth and thus the cleansing effect contributed to the granules can be organoleptically recognized. This invention was achieved based on the above findings. More particularly, the inventors found that a granular composition having a certain range of grain size and prepared by binding a water-insoluble powder material of poor polishing power having a particle diameter of 10 microns or less in maximum by the use of a water-insoluble inorganic binder, is imparted with a proper degree of polishing power and can produce a sufficient polishing power for cleansing the teeth even when the powder is very fine one. Accordingly, this invention provides a granular composition which comprises a water-insoluble powder material and a water-insoluble inorganic binder capable of binding said water-insoluble powder material, said composition having a diameter such that 80 wt % or more of the granules can pass through a No. 32 mesh of an analytical sieve but cannot pass through a No. 200 mesh of the sieve, and collapsing under a load of 0.1–10 g per one grain of granule.

BRIEF DESCRIPTION OF THE DRAWINGS

In FIG. 2, a reference numeral 5 denotes an acrylic plate, a reference numeral 6 denotes a dentifrice composition and a reference numeral 7 denotes a brush.

DETAILED DESCRIPTION OF THE INVENTION AND PREFERRED EMBODIMENTS

Figure 1:
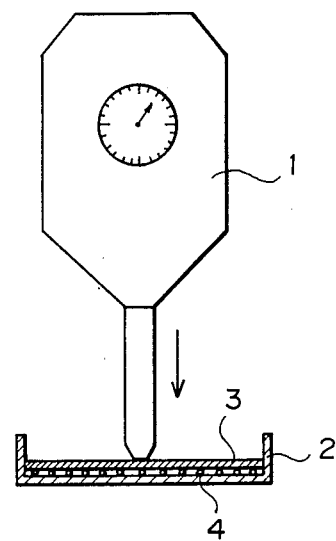
FIG. 1 is a sketch showing the device used for measuring the strength of granular grains. In this sketch are illustrated a push-pull gauge 1 which presses an acrylic plate 3 covering granules 4 which are placed in an acrylic cell 2.

The starting water-insoluble powder materials usable for preparing a granular composition of this invention are not specially limited if usable for cosmetic compositions, dentifrice, and pharmaceutical agents or the like, and may be referred to dibasic calcium phosphate, tribasic calcium phosphate, insoluble sodium metaphosphate, silica, aluminum hydroxide, magnesium phosphate, calcium carbonate, calcium pyrophosphate, zeolite, complex aluminosilicate, magnesium carbonate, red iron oxide, calcium sulfateand so on which are generally used as polishers for dentifrice. The powder should have a size distribution where particles of 80% by weight of the total amount of powder have a diameter ranging from 0.1 to 20 microns and preferably the major diameter of them should be 10 microns or less. By the granulation of small particles having a very poor polishing ability, colored particle strongly adhered on the surface of the teeth can be removed to achieve cleansing of the teeth, while after the granules collapse, the polishing ability is diminished and the tooth surface will not be damaged. Especially, when a fine powder of zeolite is used, the optimum effect will be obtainable. This is because zeolite which exhibits more enhanced ion-exchanging ability and more increased tartar deposition preventing ability as the size of the primary particle is made smaller, is further imparted with a proper polishing power by being granulated.

The binders usable for preparing a granular composition of the present invention are water-insoluble inorganic compounds. Some water-soluble and water-insoluble binders are taught by the prior art. In the prior art, however, when water-insoluble binders are used, most of them are organic materials, and inorganic binders have not yet been disclosed. In the practice of the invention, usable water-insoluble inorganic materials include colloidal silica, magnesium aluminate metasilicate, bentonite, montomorillonite, kaolin, synthesized aluminum silicate, calcium silicate, aluminum hydroxide gel, alumina sol, magnesium carbonate, synthesized hydrotalcite, magnesium oxide, magnesium hydroxide, among which silicon compounds are especially preferred. When the spray granulation is adopted for the manufacture, materials which exhibit a thixotropic property in the slurry state are easy to be processed, and from this point of view, magnesium aluminate metasilicate and colloidal silica are preferred. The granules prepared by binding by the use of these binders can maintain its solidity even when they soak humidity. The solidity can be varied according to the kind, combination and amount of binders, and preparation method of granules. The incorporation amount is, when inorganic binders having a thixotropic property and serving as vehicles such as magnesium aluminate metasilicate and synthesized aluminum silicate are used, preferably 30 wt % or more with respect to the amount of the water-insoluble powder material. If less than 30 wt %, spray conditions will be affected. In the case where inorganic binders which will greatly enhance the granular strength because of their adhesive property, such as colloidal silica and alumina sol are used, their incorporation amount is preferably from 0.5 to 30 wt % with respect to the total amount of the granules. If the incorporation amount is less than 0.5 wt %, the strength be insufficient, whereas over 30 wt %, problems will arise including deposition of the granules on the wall of spray-drying which necessitates a cumbersome cleaning work, or spray nozzle will get clogged leading to inability of the manufacture. Further, various granule compositions having a predetermined strength and containing various kinds of powder material in various amounts can be obtained by a combination use of binders which serve as vehicles and binders which have an adhesive property. The granules prepared by binding by the use of the mentioned inorganic binders possess, different from those prepared by using organic binders, a characteristic feature in that they can initially be perceived as granules in the mouth, and as they slowly collapse while giving the crispy feeling, the cleansing effect is convinced by the user. Binders aside from the above described water-insoluble inorganic binders can be incorporated unless the effect of the present invention will not be impeded. However, water-soluble organic binders and oil-soluble organic binders are not preferable, because the former ones decrease a strength of granules and the latter ones impart the unpleasant feel.

In the preparation of the granular composition of the present invention, the adjustment of its particle size is important. It has generally been known that the polishing effect of an abrasive in a dentifrice increases as the particle size of the abrasive increases up to about 30 $\mu m$, but if the particle size exceeds this range, the polishing effect would not be increased any more (COSMETIC SCIENCE, edited by M. M. BREUER, vol. 1, pages 73 to 75, 1978, ACADEMIC PRESS). It is said that this is because the abrasive particles will not be placed between the teeth and a toothbrush and will escape when the particle size is too large. Anyway, it is considered that a maximum polishing effect can be obtained by using an abrasive having a particle size of 30 $\mu m$ or more. In other words, particles which do not pass through a No. 400 analytical sieve (stipulated in JIS standard; hereinafter the same is applied) are favorable. However, the particles having a particle size of about 30 $\mu m$ are scarcely recognized with the naked eye or are quite difficult to be sensed inside the mouth. This problem can be solved by using particles which do not pass through a No. 200 analytical sieve. On the other hand, if the particle size is too large, a coarse feel is highly imparted, so that a feel of use becomes unfavorable. This problem can be solved by eliminating particles which do not pass through a No. 32 analytical sieve. Therefore, in order to obtain a sufficient polishing effect and an excellent feel of use, it is required that the granular composition has such a particle size that 80 wt % or more of the particles of the granular composition pass through a No. 32 analytical sieve and 80 wt % or more do not pass through a No. 200 analytical sieve.

In the manufacture of the granular compositions according to this invention, the strength of the granules is also important. If the granules are crashed under a load of 0.1 g or less per one grain, the granular shape will not be palpable. On the other hand, if the granules are not crashed under a load of 10 g or more, they will be felt as unpleasant foreign matter, and will not collapse along with brushing, so that they will damage the enamel layer of the teeth. Accordingly, the granules should have such strength that will collapse under a load of 0.1-10 g, more preferably 1-5 g per one grain of them. When brushing is carried out using a dentifrice in which the granular compositions of this invention are incorporated, the granules are expected to collapse along the brushing process and accordingly the polishing power will decrease. Therefore, if the primary powder is properly selected from the water-insoluble powder materials having a very poor abrasion power, it is possible to manufacture a dentifrice composition which is capable of giving a minimized harmful effect of V-shape damage in the tooth surface notwithstanding a prolonged brushing time.

A diversity of the granules having the above mentioned size distribution and strength can be prepared by changing the kind of the inorganic binders, the combination and proportion thereof, and manufacturing process of the granules.

When inorganic binders are used, a spray granulation is recommended for preparing the granular compositions of the present invention. According to the spray granulation, the final shape of the grain of the granules will become a good sphere, and accordingly, aesthetic appreciation will be expected when incorporated in the pasty material of dentifrice while giving good feel of touch in the mouth. By contrast, other processes such as extrusion granulation will produce angular grains and they will damage the tooth surface. Spherical grains as in the inventive granules will minimize such potential injury. In any case, from the viewpoints of properties and handling of the products, the spray granulation method is most advisable.

The thus obtained granular composition of the present invention can be incorporated in various moist compositions such as creams and ointments, preferably in a dentifrice.

The granular composition is incorporated in an amount of 1 to 50%, preferably 3 to 30% into a dentifrice. A dentifrice is prepared in a conventional manner, and other components usable for a common dentifrice can also be incorporated. For example, as a binding agent, sodium carboxymethyl cellulose, sodium polyacrylate, hydroxyethyl cellulose, thickening silica, montmorillonite, carrageenan, sodium alginate, guagum, pectin and the like are usable. As a surface active agent, salts of acylamino acids such as sodium acylglutamate and sodium acylsarcosinate, salts of alkyl phosphoric acids such as sodium lauryl phosphate, sucrose fatty acid esters, sorbitan fatty acid esters, polyoxyethylene fatty acid esters and the like are usable. Further, as a medicinal component, allantoin, tranexamic acid, Vitamin E, Vitamin C, sodium chloride, bittern, sodium fluoride, tin fluoride, carbazochrome, propolis, glycyrrhetinic acid, chlorohexyzine, cetylpyridinium chloride and the like are usable.

When a granular composition according to this invention is incorporated in a dentifrice composition, the granules can be recognized as granules in the mouth and cleansing or polishing effect of the teeth can be acknowledged with almost no unpleasant feel of foreign matter. Moreover, the granular composition is stable when incorporated in compositions containing much water while maintaining a certain degree of crushing force. Taking advantage of the phenomenum in which the loss in diameter along with the process of slow collapsing makes the polishing power go down, V-shape injury in the tooth surface causable from prolonged time of brushing or excessive brushing pressure can be prevented. Still moreover, a dentifrice composition prepared by using zeolite as a water-insoluble powder material is very advantageous due to its excellent tartar deposition preventing ability and coloring prevention ability.

The present invention is further explained by way of examples, which should not be construed as limiting the invention thereto.

EXAMPLE 1

(i) An aqueous slurry containing about 60% by weight of water and, as solid matters, 60 parts by weight of zeolite (type 4A) in which 99.9 wt % of particles have a maximum particle diameter of 10 microns or less, 10 parts by weight of silicic acid anhydride (colloidal silica), 2 parts by weight of titanium oxide and 28 parts by weight of magnesium aluminate metasilicate was subject to a spray granulation to prepare a granular composition. Throughout the granulation process, spray conditions were quite stable. The resultant granules had spherical grains with a smooth surface, and 92 wt % of the granules could pass a mesh No. 32 and couldn't pass a mesh No. 200 of an analytical sieve. The granules were classified by screens and a certain number (100–200) of grains having the same size of about 200 microns were placed in an acrylic cell so as to form a single layer of the granules as shown in FIG. 1, followed by covering with an acrylic plate, and loaded by a push-pull gauge to measure the load of collapsing point of the granules. The load value was divided by the number of the grains of the granules used in the test and the load per one granule was obtained to represent the strength of the granules.

(ii) Next, in order to examine the stability of the granules in an aqueous system, 3.0 g of the granules were taken and placed in a 30 ml vial to which 25 ml of purified water was added and sealed, and allowed to stand for one day. Thereafter, an iron ball having a diameter of 7 mm and weighing 3.6 g was placed in the vial, sealed again and shaken by a shaking machine for 5 minutes. This operation is called "pulverizing treatment". After the treatment, the content of the vial was transferred on a No. 200 mesh sieve. The iron ball was removed and the granular materials having a grain size of 75 microns or less was excluded under running water. Granules remained on the sieve were taken and dried at 110° C. for 2 hours to measure the mass. The data are shown in Table 2 below.

(iii) In order to make organoleptic evaluations of the granules, those having a diameter ranging from 200–300 microns were incorporated in a dentifrice composition formulated according to Table 1. The dentifrice composition was allowed to stand for one week for stabilization of the perfume. Thereafter, a panel consisting of 20 people used the dentifrice composition and evaluated the palpability of the granules contained therein immediately after using it. The toothbrushes used were normal round-cut brushes. The evaluation was carried out in accordance with the following 3 grades:

1 . . . granules are perceived throughout the brushing process,
2 . . . granules are perceived initially but the perception dissipates during the brushing process,
3. . . . granules cannot be perceived. As to the touch of granules, evaluation was made according to the following 5 grades:
1 . . . good
2 . . . fair
3 . . . moderate
4 . . . slightly bad
5 . . . bad

TABLE 1

| Ingredients | wt % |
|---|---|
| Granular composition | 15.0 |
| glycerine | 10.0 |
| solbitol solution | 30.0 |
| iotacarageenan | 2.0 |
| sodium lauryl sulfate | 1.2 |
| sodium saccharide | 0.1 |
| methyl paraben | 0.1 |
| perfume | 0.8 |
| purified water | balance |
| Total: | 100.0 |

EXAMPLE 2

An aqueous slurry containing, as solid matters, 60 parts by weight of dibasic calcium phosphate in which 85 wt % of particles have a maximum particle diameter of 10 microns or less, 10 parts by weight of silicic acid anhydride (colloidal silica), 2 parts by weight of titanium oxide and 28 part by weight of magnesium aluminate metasilicate was subject to a spray granulation to prepare a granular composition. Throughout the granulation process, spray conditions were quite stable. The resultant granules had spherical grains with a smooth surface, and 90 wt % or more of the granules could pass a mesh No. 32 and couldn't pass a mesh No. 200 of an analytical sieve. The strength of the granules, stability and strength in an aqueous system, and the touch when incorporated in a dentifrice composition were tested in the similar manner as in Example 1.

EXAMPLE 3

An aqueous slurry containing about 60% by weight of water and, as solid matters, 60 parts by weight of zeolite (type 4A) in which 85 wt % of particles have a maximum particle diameter of 10 microns or less, 38 parts by weight of magnesium aluminate metasilicate and 2 parts by weight of titanium oxide was subject to a spray granulation to prepare a granular composition. Throughout the granulation process, spray conditions were quite stable. The resultant granules had spherical grains with a smooth surface, and 87 wt % of the granules could pass a mesh No. 32 and could not pass a mesh No. 200 of an analytical sieve. The strength of the granules, stability and strength i an aqueous system, and the touch when incorporated in a dentifrice composition were tested in the similar manner as in Example 1.

COMPARATIVE EXAMPLE 1

An aqueous slurry containing, as solid matters, 60 parts by weight of dibasic calcium phosphate in which 85 wt % of particles have a maximum particle diameter of 10 microns or less, 35 parts by weight of magnesium aluminate metasilicate and 5 parts by weight of a salt of carboxymethyl cellulose was subject to a spray granulation to prepare a granular composition. Throughout the granulation process, spray conditions were quite stable. The resultant granules had spherical grains with a smooth surface, and 87 wt % of the granules could pass a mesh No. 32 and couldn't pass a mesh No. 200 of an analytical sieve. The strength of the granules, stability and strength in an aqueous system, and the touch when incorporated in a dentifrice composition were tested in the similar manner as in Example 1.

COMPARATIVE EXAMPLE 2

An aqueous slurry containing, as solid matters, 30 parts by weight of zeolite (type 4A) in which 99.9 wt % of particles have a maximum particle diameter of 10 microns or less, 30 parts by weight of magnesium aluminate metasilicate, 20 parts by weight of alumina sol and 20 parts by weight of silicic acid anhydride (colloidal silica) was subject to a spray granulation to prepare a granular composition. During the granulation process, spray conditions slowly got worse and finally the pump motor got out of order due to the clogged spray nozzle, thus the manufacture was compelled to stop. The granules obtained before the stoppage had spherical grains with a smooth surface, and 87 wt % of the granules could pass a mesh No. 32 and could not pass a mesh No. 200 of an analytical sieve. The strength of the granules, stability and strength in an aqueous system, and the touch when incorporated in a dentifrice composition were tested in the similar manner as in Example 1.

COMPARATIVE EXAMPLE 3

60 parts by weight of dibasic calcium phosphate in which 85 wt % of particles have a maximum particle diameter of 10 microns or less, 3 parts by weight of ethyl cellulose were taken as solid matters, and an appropriate amount of acetone was added thereto and mixed. The mixture was formed into granules by an extrusion granulation process to prepare granules. The resultant granules had grains in an almost cylindrical shape with an angular surface, and 84 wt % or more of the granules could pass a mesh No. 32 and could not pass a mesh No. 200 of an analytical sieve. The strength of the granules, stability and strength in an aqueous system, and the touch when incorporated in a dentifrice composition were tested in the similar manner as in Example 1.

TABLE 2

| | | Example 1 | Example 2 | Example 3 | Comparative Example 1 | Comparative Example 2 | Comparative Example 3 |
|---|---|---|---|---|---|---|---|
| Strength of the granules (g/grain) | | 2.21 | 1.43 | 0.83 | 0.005 or less (impossible to measure) | 11.30 | 1.31 |
| Remaining granules after pulverizing treatment (initial: 3.0 g) | | 2.27 | 2.03 | 1.82 | impossible to measure*1 | 2.70 | 1.78 |
| Granules | (1) | 4 | 2 | 1 | 0 | 12 | 3 |
| Percieved | (2) | 16 | 15 | 14 | 5 | 8 | 16 |
| (number of people) | (3) | 0 | 3 | 5 | 15 | 0 | 1 |
| Touch of the | (1) | 4 | 1 | 2 | 0 | 2 | 0 |
| granules*2 | (2) | 11 | 11 | 8 | 0 | 0 | 2 |
| (number of | (3) | 4 | 3 | 3 | 4 | 2 | 6 |
| people) | (4) | 1 | 2 | 2 | 1 | 2 | 9 |
| | (5) | 0 | 0 | 0 | 0 | 14 | 2 |

*1: Granules of Comparative Example 1 were greatly softened when placed in water and so many granules aggregated with each other that made the measurement impossible. Apparently, the strength of the granules was declined because they were in the state of swelling.
*2: People who did not perceive the granules were not asked about the touch of them.

EXPERIMENT 1

Figure 2:
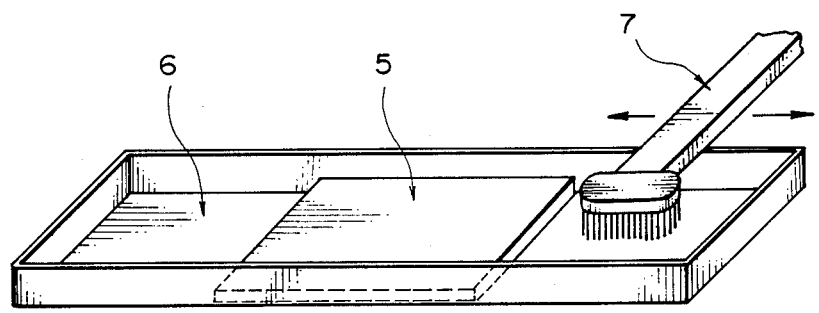
FIG. 2 is a perspective sketch of a brushing machine used in Experiment 1.
Figure 3:
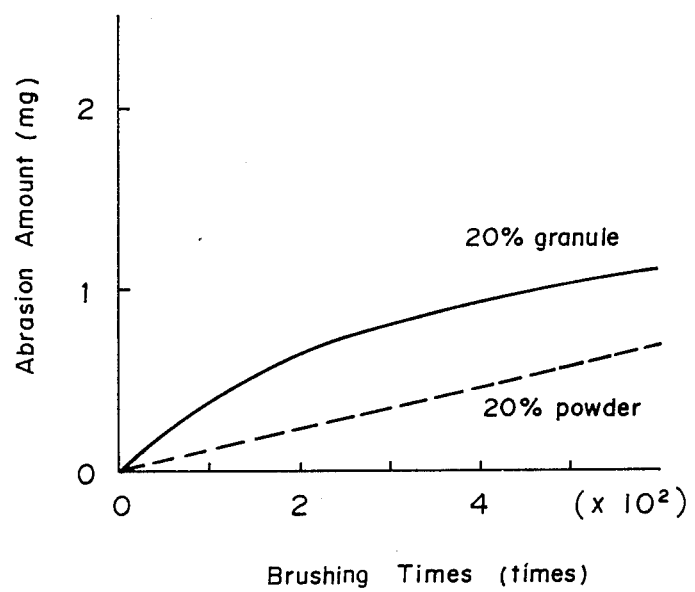
FIG. 3 is a graph showing the relation of abrasion amount of acrylic plate and the brushing times.

A dentifrice composition blended with a granular composition of the present invention was compared with a referential powder product in terms of the polishing power. As shown in FIG. 2, an acrylic plate was set in a brushing machine. The dentifrice compositions were made into aqueous 50 wt % solution by being diluted with water, and 150 ml of the solution was placed in the brushing machine. The brushing was carried out while undergoing a 640 g load. After a determined period of time, the acrylic plate upon which the brushing was carried out was measured to obtain the loss of the plate by abrasion. The dentifrice compositions used in this experiment are shown in Table 3 below, and the results are illustrated in FIG. 3.

TABLE 3

| Ingredients | Inventive composition | Comparative composition |
|---|---|---|
| granular composition obtained in Ex. 3 | 20.0 (wt %) | — (wt %) |
| starting powder* | — | 20.0 |
| glycerine | 10.0 | 10.0 |
| solbitol solution | 20.0 | 20.0 |
| iota carageenan | 2.0 | 2.0 |
| sodium lauryl sulfate | 1.2 | 1.2 |
| sodium saccharide | 0.1 | 0.1 |
| methyl paraben | 0.1 | 0.1 |
| perfume | 0.8 | 0.8 |
| purified water | balance | balance |
| Total | 100% | 100% |

Starting power*: Powder having the same conposition as the granular composition of Example 3. In other words, this is obtained by simply mixing the starting materials of the granular composition.

As seen from FIG. 3, the inventive composition (granule) has higher polishing power than the referential powder product, and has a characteristic feature in that the polishing power is declined along with the brushing process to finally have power of about the same level as the powder product.

EXPERIMENT 2

A dentifrice composition formulated according to Table 3 was prepared and its cleansing power was tested. A glass plate was coated by a black marking ink (Tradename: Magic Ink) and the glass was brushed with a toothbrush applied with 1 g of a sample composition. The number of brushing times until the ink was completely removed was checked. The results are shown in Table 4.

TABLE 4

| Test Sample | Polishing Power (Average of 10 times) |
|---|---|
| Inventive composition | 5.3 times |
| Comparative composition | 35.7 times |

The data indicate that the inventive granular composition has a high polishing ability that is not possessed by the starting material of zeolite powder, and exhibits an excellent cleansing power.

What is claimed is:

1. A granular composition, which comprises a water-soluble powder material selected from the group consisting of dibasic calcium phosphate, tribasic calcium phosphate, insoluble sodium metaphosphate, silica, aluminum hydroxide, magnesium phosphate, calcium carbonate, calcium pyrophosphate, zeolite, complex aluminosilicate, magnesium carbonate, red iron oxide, calcium sulfate and a mixture of two or more of them and a binder selected from the group consisting of colloidal silica, magnesium aluminate metasilicate, bentonite, montmorillonite, synthesized aluminum silicate, calcium silicate, aluminum hydroxide gel, alumina sol, magnesium carbonate, synthetic hydrotalcite, magnesium oxide, magnesium hydroxide and a mixture of two or more of the same; said composition containing granules having a diameter such that 80 wt. % or more of the granules are capable of passing through a No. 32 mesh of an analytical sieve, but are incapable of passing through No. 200 mesh of the sieve, and which collapse under a load of 0.1–10 g. per grain of granule.

2. The granule composition according to claim 1, wherein said granules have a substantially spherical shape.

3. The granular composition according to claim 1 which is obtained by a spray granulation process.

4. The granular composition according to claim 1, wherein said water-insoluble powder material has a particle size distribution such that particles having a diameter of 10 microns or less occupy 80 wt. % or more of the total amount of powder.

5. The granular composition according to claim 1 further comprises 0.01 to 10 wt. % of a coloring agent.

6. The granular composition according to claim 5 wherein said coloring agent is ultramarine or titanium oxide.

7. The granular composition according to claim 1 wherein said water-insoluble powder material is zeolite.

8. The granular composition according to claim 1 wherein said water-insoluble inorganic binder is selected from the group consisting of colloidal silicia, magnesium aluminate metasilicate, bentonite, montmorillonite, kaolin, synthesized aluminum silicate, calcium silicate, aluminum hydroxide gel, alumina sol, magnesium carbonate, synthesized hydrotalcite, magnesium oxide, magnesium hydroxide and a mixture of two or more of them.

9. The granular composition according to claim 1 wherein said water-insoluble inorganic binder is silicon compound.

10. The granular composition according to claim 1 wherein said water-insoluble inorganic binder is magnesium aluminate metasilicate and colloidal silica.

11. The dentifrice composition according to claim 1 wherein said granular composition comprises 1–50 wt % of the total composition.

12. A dentifrice composition, which contains a granular composition comprising a water-insoluble powder material selected from the group consisting of dibasic calcium phosphate, tribasic calcium phosphate, insoluble sodium metaphosphate, silica, aluminum hydroxide, magnesium phosphate, calcium carbonate, calcium pyrophosphate, zeolite, complex aluminosilicate, magnesium carbonate, red iron oxide, calcium sulfate and a mixture of two or more of them and a binder selected from the group consisting of colloidal silica, magnesium aluminate metasilicate, bentonite, montmorillonite, synthesized aluminum silicate, calcium silicate, aluminum hydroxide gel, alumina sol, magnesium carbonate, synthetic hydrotalcite, magnesium oxide, magnesium hydroxide and a mixture of two or more of the same; said composition containing granules having a diameter such that 80 wt. % or more of the granules are capable of passing through a No. 32 mesh of an analytical sieve, but are incapable of passing through a No. 200 mesh of the sieve, and which collapse under a load of 0.1–10 g. per one grain of granule.

13. The granular composition according to claim 1, which contains granules which collapse under a load of 1 to 5 g. per one grain of granule.

14. The dentifrice composition according to claim 12, wherein said granular composition comprises 3 to 30 wt. % of the total composition.

* * * * *

UNITED STATES PATENT AND TRADEMARK OFFICE
CERTIFICATE OF CORRECTION

PATENT NO. : 4,871,396

DATED : OCTOBER 3, 1989

INVENTOR(S) : Satoshi TSUJITA et al

It is certified that error appears in the above-identified patent and that said Letters Patent is hereby corrected as shown below:

Column 9, lines 53 and 54:  "water-soluble" should read
-- water-insoluble --.

Signed and Sealed this

Twenty-first Day of April, 1992

Attest:

HARRY F. MANBECK, JR.

Attesting Officer      Commissioner of Patents and Trademarks